United States Patent [19]

Amemiya

[11] Patent Number: Plant 6,205

[45] **Date of Patent: * Jun. 21, 1988**

[54] *CLIVIA MINIATA* CV. MONYA

[75] Inventor: Hodge Amemiya, Torrance, Calif.

[73] Assignee: Monrovia Nursery Company, Azusa, Calif.

[ * ] Notice: The portion of the term of this patent subsequent to Jun. 21, 2004 has been disclaimed.

[21] Appl. No.: 621,799

[22] Filed: Jun. 18, 1984

[51] Int. Cl.[4] ..... A01H 5/00

[52] U.S. Cl. ..... Plt./68

[58] Field of Search ..... Plt. 68

*Primary Examiner*—Robert E. Bagwill

[57] ABSTRACT

A new and distinct selection of *Clivia miniata* Regel (popularly known as the Kaffir Lily) which hereinafter shall be referred to as *Clivia miniata* cultivar Monya. *Clivia miniata* cv. Monya differs from seedlings by possessing a combination of broader foliage, a larger number of flowers in the inflorescence, individual flowers a darker and more red color, and individual flowers possessing tepals which are consistent in size.

1 Drawing Sheet

DISCOVERY

This invention relates to a new and distinct selection of *Clivia miniata*, a member of the Amaryllis family, Amaryllidaceae. *Clivia miniata* cv. Monya as discovered in a cultivated state in a garden by me at a private residence in Inglewood, Calif. in the Spring of 1953.

The plant to date is known to exist only within the boundaries of Monrovia Nursery, 18331 E. Foothill Boulevard, Azusa, Calif. and Mariposa Nursery, 932 Beach Street, Montebello, Calif. This selection has not been offered for sale or described in any publication.

REPRODUCTION

This new selection has been strictly asexually reproduced by divisions at Mariposa Nursery in order to retain the characteristics of broad foliage, a dense inflorescence comprised of more flowers, flowers that are a darker and more red color and flowers that possess tepals which are consistent in size. Sexual reproduction, such as seed propagation, could result in a potential loss of the selected attributes. Therefore, sexual reproduction is prohibited and propagation is restricted to asexual reproduction by division. Seed progeny from the new selection has been observed but produces a plant with variable characteristics.

CHARACTERISTICS

*Clivia miniata* cv. Monya differs from unselected seedlings by possessing a combination of unique characteristics listed below:

1. The foliage on the new selection is broader, in a range of 9 cm to 7 cm wide. The seedlings have a much more variable range, from 4½ cm and wider with an average leaf width of 6 cm.

2. *Clivia miniata* cv. Monya has more flowers in an inflorescence, from 16 to 31 flowers with an average of 24 flowers per umbel. The seedlings have fewer flowers, averaging 14 per inflorescence. The more numerous flowers in our selection results in a much more fuller and denser inflorescence. (see FIG. 1).

3. The selection also differs in that the individual flowers are a darker and more consistent color. The selection color is a Capsicum Red on the outside of tepals and a Dutch Vermillion on inside of the tepals. The seedling plants possess flowers which are a wide range of colors, from dark red to light orange—Fire Red 15/1 to Marigold Orange 11/2 (see FIG. 2).

4. Individual flowers on the selection have broader tepals and tepals which are a consistent length. The length of tepals on the selection measure 6 cm±2 mm whereas the seedling length varies from 5.4 cm to 8.5 cm. The tepal width also varies considerably in the seedling. This variable length and width of tepals is clearly demonstrated with an overall side view of the perianth (see FIG. 2).

On the new selection the base of the perianth (which is the red portion of the flower just above the ovary) measures 0.6 cm, the widest portion (the uppermost part of the perianth) measures 6.3 cm. The seedlings are variable ranging from 0.6–0.7 cm at the base of the perianth to 4–9 cm at the uppermost part of the perianth.

These combinations produce a unique selection with a more uniform color and denser habit and appearance.

BRIEF DESCRIPTION OF THE DRAWING

The above photo, FIG. 1, labeled selection shows a specimen of the selected plant exhibiting the wide leaf size and dense inflorescence, along with the dark consistent color of the tepals.

The photo below, FIG. 2, designated prior art and selection depicts individual flowers of seedlings above the ruler and flowers of the new selection below. Clearly shown are the consistent color, length and width of the tepals of my selection and the variation of seedling flowers.

DESCRIPTION

Below is a detailed description of the new selection, all color terminology is derived from the British Horticultural Colour Charts:

Overall size and habit: Approximately 2 feet in height, large leathery two-ranked strap-like leaves, inflorescence arising from center of plant.

Inflorescence: Composed of an umbel on a scape (Leafless stalk).

Scape:

*Length.*—28 cm to 36 cm.

*Width.*—At the most narrow portion 3 to 4 cm.

Flower:

*Width.*—5.5 to 6.3 cm.
*Length.*—5.8 to 6 cm.
*Shape.*—Funnelform.
*Number in inflorescence.*—16 to 31, average number 24.

Flower segments (tepals):
*Number.*—Six.
*Length.*—6 cm±2 mm.
*Width.*—3 Inner tepals broader 2.5 cm±2 mm. 3 outer tepals narrower 1.8 cm±2 mm.
*Color.*—Outside tepals: Capsicum Red 715. Inside tepals: Dutch vermilion 717. Base of inside tepals and lower half of filaments: Chrome Yellow 605/2. 3 inner tepals white markings on lower ½ of margins.

Leaf:

*Shape.*—Ligulate.
*Width.*—7 to 9.5 cm at broadest portion.
*Length.*—45.5 to 61 cm.
*Arrangement.*—Opposite, 2 ranked.
*Color.*—Upper side of leaf Ivy Green 0001060/3. Lower side of leaf Spinach Green 0960/1.

I claim:

1. A new and distinct selection of *Clivia miniata* as substantially shown and described herein, characterized particularly as to novelty by the unique combination of broader foliage, a denser inflorescence comprised of more flowers, individual flowers a darker and more red color and individual flowers possessing tepals which are consistent in size.

* * * * *

FIG. 1
SELECTION
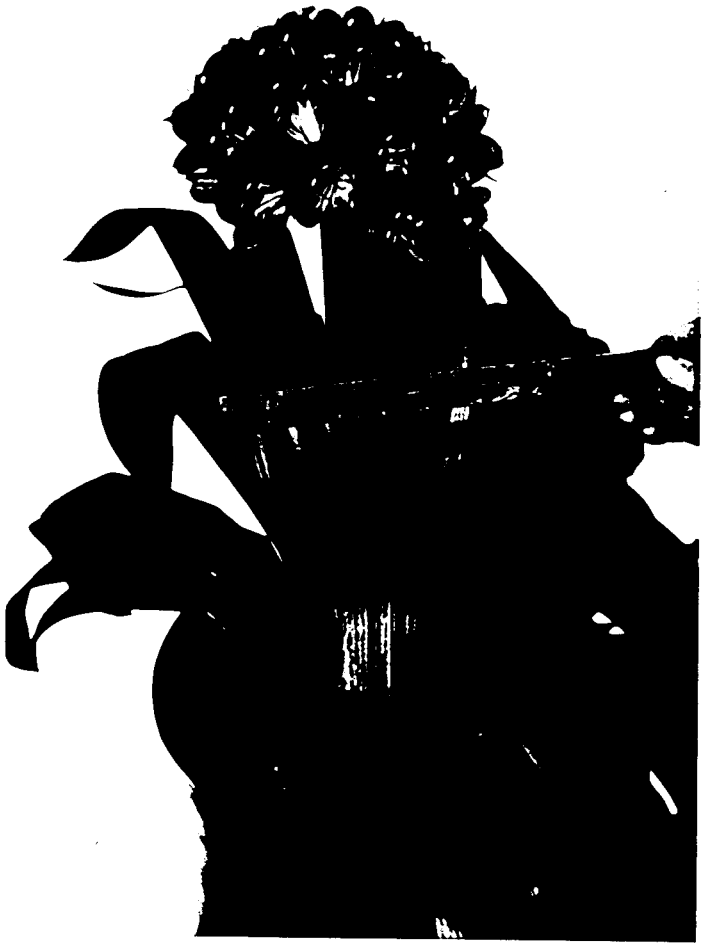
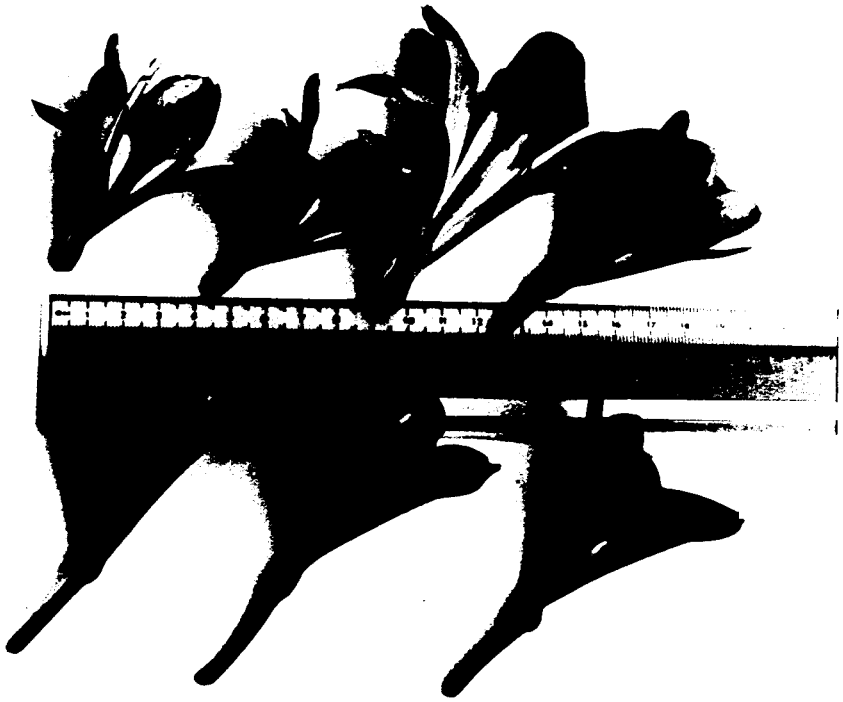
PRIOR ART
FIG. 2